United States Patent [19]

Jonas et al.

[11] 4,260,628
[45] Apr. 7, 1981

[54] 2-GUANIDINOMETHYL-INDOLINES

[75] Inventors: Rochus Jonas, Darmstadt; Hans-Jochen Schliep, Traisa; Ernst Schorscher, Darmstadt-Arneilgen, all of Fed. Rep. of Germany

[73] Assignee: Merck Patent Gesellschaft mit beschränkter Haftung, Darmstadt, Fed. Rep. of Germany

[21] Appl. No.: 78,855

[22] Filed: Sep. 26, 1979

Related U.S. Application Data

[62] Division of Ser. No. 939,046, Sep. 1, 1978, abandoned.

[30] Foreign Application Priority Data

Sep. 3, 1977 [DE] Fed. Rep. of Germany ....... 2739723

[51] Int. Cl.³ .................... A61K 31/40; C07D 209/14
[52] U.S. Cl. ..................... 424/274; 260/326.11 R; 260/326.15; 424/232; 424/266
[58] Field of Search ................. 260/326.11 R, 326.15; 424/274

[56] References Cited

U.S. PATENT DOCUMENTS

| 3,317,560 | 5/1967 | Claassen | 260/326.15 |
| 3,354,174 | 11/1967 | Bell | 260/326.11 R |
| 3,428,653 | 2/1969 | Bell | 260/326.15 |
| 3,853,878 | 12/1974 | Jonas et al. | 260/326.11 R |

FOREIGN PATENT DOCUMENTS

2608186  9/1976  Fed. Rep. of Germany ....... 260/239 B

*Primary Examiner*—Alton D. Rollins
*Attorney, Agent, or Firm*—Millen & White

[57] ABSTRACT

2-Guanidinomethyl-indolines of the formula

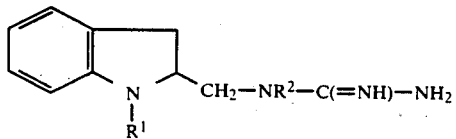

(I)

wherein $R^1$ and $R^2$ each independently is H or alkyl of 1-6 carbon atoms, and the physiologically acceptable acid addition salts thereof have good antihypertensive properties.

10 Claims, No Drawings

2-GUANIDINOMETHYL-INDOLINES

This is a division of application Ser. No. 939,046 filed Sept. 1, 1978, now abandoned.

BACKGROUND OF THE INVENTION

The present invention relates to indoline derivatives having pharmacological activity.

SUMMARY OF THE INVENTION

It is an object of this invention to provide novel compounds which can be used for the preparation of medicaments, e.g., having anti-hypertensive effects.

Upon further study of the specification and appended claims, further objects and advantages of this invention will become apparent to those skilled in the art.

These objects have been attained by providing 2-guanidinomethyl-indolines of formula I

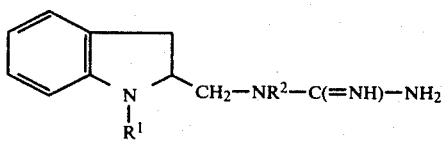

in which $R^1$ and $R^2$ each independently is H or alkyl of 1–6 carbon atoms, and their physiologically acceptable acid addition salts.

DETAILED DISCUSSION

In formula I, the radicals $R^1$ and $R^2$, which can be identical or different, are preferably H or alkyl of 1–3 carbon atoms, especially H, methyl or ethyl and also n-propyl or isopropyl; and, moreover, butyl, such as n-butyl, isobutyl, sec-butyl, or tert-butyl, pentyl, such as n-pentyl, isopentyl or neopentyl, or hexyl, such as n-hexyl or isohexyl are also suitable.

The present invention also relates to processes for the preparation of the compounds of formula I, which comprise (a) reacting a 2-aminomethylindoline of formula II

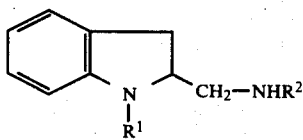

in which $R^1$ and $R^2$ are as defined for formula I, or an acid addition salt of such a compound, with a compound of formula III $$NR^3=CR^4-NH_2 \qquad (III)$$

in which $R^3$ is H and $R^4$ is alkoxy, alkylmercapto, 3,5-dialkyl-1-pyrazolyl (in which the alkyl groups each have 1–4 carbon atoms) or NC—NH—, or $R^3$ and $R^4$ together are a C–N bond, or with an acid addition salt of such a compound;

(b) treating with a reducing agent a compound which corresponds to formula I except that in place of one or more H atoms there is one or more groups detachable by reduction and/or one or more double bonds, such compounds especially including compounds, which differ from I, of formula IV

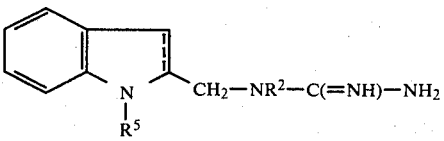

in which an additional C–C bond can be present in the position indicated by the dotted line, $R^5$ is a radical detachable by hydrogenolysis, especially benzyl, or is $R^1$, and $R^1$ and $R^2$ are as defined for formula I, or an acid addition salt of such a compound; or (c) if appropriate, converting the resulting compound by treatment with an acid into a physiologically acceptable acid addition salt.

In other respects, the compounds of formula I are prepared by methods known per se, such as are described in the literature (for example, in the standard works, such as Houben-Weyl, Methoden der Organischen Chemie (Methods of Organic Chemistry), Georg-Thieme-Verlag, Stuttgart; Organic Reactions, John Wiley & Sons, Inc., New York) and specifically are prepared under the reaction conditions which are known and suitable for the said reactions. It is also possible to make use of conventional variants of these reactions which are known per se and are not mentioned in greater detail here.

The compounds of formula I are preferably prepared by reaction of the compounds of formulae II and III.

The 2-aminomethylindolines of formula II are novel; they can, however, be prepared by methods known per se. For example, indoline-2-carboxylic acid esters can be reduced with LiAlH$_4$ to 2-hydroxymethylindolines and these can be reacted with SOCl$_2$ or PBr$_3$ to give 2-chloromethyl- or 2-bromomethyl-indolines. Reaction with potassium phthalimide and subsequent solvolysis results in the 2-aminomethylindolines of the formula II ($R^2$=H). The 2-aminomethylindolines of the formula II ($R^2$=alkyl having 1–6 carbon atoms) are obtainable therefrom by conventional alkylation or acylation (for example, acetylation) and subsequent conventional reduction.

The compounds of formula III are generally known and include, in particular, cyanamide, dicyandiamide, O-alkyl-isoureas, S-alkylisothioureas or 3,5-dialkyl-pyrazole-1-carboxyamidines in which the alkyl groups have 1–4 carbon atoms but preferably are methyl.

Preferred compounds are the S-alkylisothioureas and, especially for the preparation of compounds of formula I in which $R^2$ is alkyl having 1–6 carbon atoms, cyanamide.

Suitable starting materials of formula IV include, in particular, indole derivative in which the dotted line signifies an additional C–C bond and $R^5$ is $R^1$, and also indoline derivatives in which $R^5$ is a radical removable by hydrogenolysis, for example benzyl or substituted benzyl groups, such as tolylmethyl, diphenylmethyl or carbobenzoxy. The compounds of formula IV are novel; they are obtainable analogously to the compounds of formula II when 1-$R^5$-indole- or 1-$R^5$-indoline-2-carboxylic acid esters are used as the starting materials.

Suitable acid addition salts of the compounds of formulae II, III and IV include, for example, the hydrochlorides, sulphates or nitrates thereof.

A compound of formula I is prepared, for example, by reacting an amine II, as the base or in the form of the sulphate or of another salt, with cyanamide in the melt at temperatures between 100° and 200° C., preferably between 110° and 150° C., or in an inert solvent, for example, hydrocarbons, such as benzene or toluene; alcohols, such as methanol, ethanol, propanol or butanol; high-boiling ethers, such as ethylene glycol monoalkyl or dialkyl ethers; water; or alcohol/water mixtures; at temperatures between about 20° C. and the boiling point of the solvent, especially between about 110° and about 150° C. In place of cyanamide, dicyandiamide can also be used in the reaction, under otherwise identical conditions. Cyanamide is then formed in situ.

A compound of formula I can also be obtained by reacting an amine II with an acid addition salt of an S-alkyl-isothiourea or of an O-alkyl-isourea, preferably in the presence of an inert solvent, such as water, acetone, dioxane or alcohols and also other water-miscible solvents. For this reaction, it is not necessary to maintain a specific temperature and the reaction can proceed, for example, at temperatures between 0° C. and the boiling point of the solvent. Furthermore, a compound of formula II can be reacted with a salt of a 3,5-dialkylpyrazole-1-carboxamidine, for example 3,5-dimethylpyrazole-1-carboxamidine nitrate, preferably in an inert solvent, such as water or alcohols or other water-miscible solvents, or without a solvent, at temperatures between 50° and 150° C., to give a compound of formula I.

Furthermore, a compound of formula IV, or an acid addition salt of such a compound, can also be reduced chemically or catalytically, to a compound of formula I (or to an acid addition salt of I).

The chemical reduction can preferably be carried out with sodium borohydride in acetic acid or with diborane in hydrocarbons, ethers, cyclic ethers, especially dioxane or tetrahydrofuran, or acetic acid, at temperatures between −70° and +100° C., preferably between −40° and +40° C.

The catalytic reduction can be carried out, for example, in the presence of catalysts, such as platinum, nickel, copper, palladium or salts thereof, in solvents, such as alcohols, dioxane, ethyl acetate or acetic acid, preferably in acetic acid/hydrochloric acid with palladium/barium sulphate. N-Benzyl groups are detached hydrogenolytically, preferably on palladium/charcoal. The temperatures are preferably between about 0° and 100° C. and especially between about 40° and about 70° C., and the reaction can be carried out either at normal pressure or under elevated pressure (up to about 200 atmospheres).

A free base of formula I, obtained according to the invention, can be converted with an acid to the corresponding acid addition salt. Depending on the amount of acid added, the mono- or di-acid addition salts can be obtained, for example, mono- or di-hydrochlorides, or hemisulphates or sulphates. Acids suitable for this reaction are those which give physiologically acceptable salts. Thus, suitable acids include inorganic acids or organic acids, for example, aliphatic, alicyclic, aromatic, araliphatic or heterocyclic monobasic or polybasic carboxylic acids or sulphonic acids. These individually include, for example, hydrochloric acid, hydrobromic acid, sulphuric acid, phosphoric acid, such as orthophosphoric acid, nitric acid, formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicyclic acid, 2-phenylpropionic acid, citric acid, gluconic acid, ascorbic acid, nicotinic acid, isonicotinic acid, methane- or ethane-sulphonic acid, ethanedisulphonic acid, 2-hydroxyethanesulphonic acid, benzenesulphonic acid, p-toluenesulphonic acid and naphthalene-mono- and -di-sulphonic acids.

The free bases of formula I can, if desired, be liberated from their salts by treatment with strong bases, such as sodium hydroxide, potassium hydroxide, sodium carbonate or potassium carbonate.

The compounds of formula I may possess one or more centers of asymmetry. They can therefore be prepared as racemates or, if optically active starting materials are used, also in an optically active form.

If the compounds have two or more centers of asymmetry, they are generally obtained from their synthesis in the form of mixtures of racemates, from which the individual racemates can be isolated in the pure form, for example, by recrystallization from inert solvents.

The resulting racemates can, if desired, be resolved mechanically or chemically into their optical antipodes, according to fully conventional methods. Preferably, diastereomers are formed from the racemates by reaction with an optically active resolving agent. Suitable resolving agents include, for example, optically active acids, such as tartaric acid, dibenzoyltartaric acid, diacetyltartaric acid, camphorsulphonic acids, mandelic acid, malic acid and lactic acid.

It has been found that the compounds of formula I and their physiologically acceptable acid addition salts possess valuable pharmacological properties, coupled with good tolerance. Thus, for example, effects on circulation are displayed, especially hypotensive effects. For example, in a long term test in daily doses above 1 mg/kg, e.g., 1–8 mg/kg administered perorally, the substances have a dosage-dependent hypotensive action on conscious nephrogenically hypertensive dogs (for the method, compare, for example, Zeitschrift f. ges. exptl. Med., Volume 130, page 513 at seq. (1959)). In the case of malignant hypertension in dogs (blood pressure: systolic 240 mm Hg or higher; diastolic 150 mm or higher), higher daily doses, e.g., 4–8 mg/kg have a life-saving effect on the animals.

The compounds of formula I and their physiologically acceptable acid addition salts can therefore be used as medicaments in human medicine and veterinary medicine and also as intermediate products for the preparation of other medicaments.

The novel compounds of formula I and their physiologically acceptable acid addition salts can be used for the preparation of pharmaceutical formulations, by bringing them into a suitable dosage form, together with at least one excipient carrier or auxiliary and optionally together with one or more other active compounds. The formulations thus obtained can be used as medicaments in human medicine or veterinary medicine, e.g., for mammals.

Suitable excipients which can be used include organic or inorganic substances which are suitable for enteral or parenteral administration or for topical application and do not react with the novel compounds, for example, water, vegetable oils, benzyl alcohols, polyethylene glycols, gelatine, carbohydrates, such as lactose or starch, magnesium stearate, talc and white petroleum jelly. In particular tablets, dragees, capsules, syrups, elixirs, drops or suppositories are used for enteral administration; solutions, preferably oily or aqueous solutions, and also suspensions, emulsions or implants are used for parenteral administration: and ointments, creams or powders are used for topical application. The novel compounds can also be lyophilized and the resulting lyophilizates can be used, for example, to prepare injection formulations. Such formulations can be sterilized and/or contain auxiliary agents, such as lubricants, preservatives, stabilizers and/or wetting agents, emulsifiers, salts for influencing the osmotic pressure, buffer substances, dyestuffs, flavorings and/or aroma generating substances. They can, if desired, also contain one or more other active compounds.

The substances according to the invention are generally administered analogously to known anti-hypertensive agents available commercially (for example, guanethidine), preferably in dosages of between about 1 and 100 mg and especially between 5 and 50 mg per dosage unit. The daily dose is preferably between about 0.02 and 5 mg/kg of body weight. The particular dose for each individual patient depends, however, on very diverse, conventional factors, for example, on the effectiveness of the particular compound employed, on the age, body weight, general state of health, sex and diet of the host, on the time and route of administration, on the rate of excretion, on the combination of medicaments employed and on the severity of the particular disease to which the therapy applies. Oral administration is preferred.

Without further elaboration, it is believed that one skilled in the art can, using the preceding description, utilize the present invention to its fullest extent. The following preferred specific embodiments are, therefor, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Each of the compounds of formula I mentioned in the Examples which follow is particularly suitable for the preparation of pharmaceutical formulations.

EXAMPLE 1

A solution of 22.4 g of S-methyl-isothiourea hemisulphate in 50 ml of water is added to a solution of 17.6 g of 1-ethyl-2-aminomethyl-indoline (obtainable by N-ethylation of ethyl indoline-2-carboxylate to give ethyl 1-ethyl-indoline-2-carboxylate, reduction of the latter with LiAlH$_4$ to give 1-ethyl-2-hydroxymethyl-indoline, reaction thereof with SOCl$_2$ to give 1-ethyl-2-chloromethyl-indoline, reaction of this compound with potassium phthalimide to give 1-ethyl-2-phthalimidomethyl-indoline and hydrolysis of the latter) in 60 ml of ethanol, and the mixture is stirred for two days at 20° C. The mixture is cooled and filtered, the product is washed with acetone and 1-ethyl-2-guanidinomethyl-indoline is obtained in the form of the hemisulphate, m.p. 199° C. The free base (oil) is obtainable therefrom using sodium hydroxide solution.

EXAMPLES 2 TO 10

The following compounds are obtaind analogously to Example 1 from 2-aminomethylindoline and 1-methyl-, 1-n-propyl-, 1-isopropyl-, 1-n-butyl, 1-isobutyl-, 1-n-pentyl-, 1-isopentyl- or 1-n-hexyl-2-aminomethylindoline:

2. 2-Guanidinomethyl-indoline.
3. 1-Methyl-2-guanidinomethyl-indoline, hemisulphate, m.p. 200° C.
4. 1-n-Propyl-2-guanidinomethyl-indoline.
5. 1-Isopropyl-2-guanidinomethyl-indoline.
6. 1-n-Butyl-2-guanidinomethyl-indoline.
7. 1-Isobutyl-2-guanidinomethyl-indoline.
8. 1-n-Pentyl-2-guanidinomethyl-indoline.
9. 1-Isopentyl-2-guanidinomethyl-indoline.
10. 1-n-Hexyl-2-guanidinomethyl-indoline.

EXAMPLE 11

Sulphuric acid is added to a solution of 20.4 g of 1-ethyl-2-ethylaminomethyl-indoline (obtainable from 1-ethyl-2-chloromethyl-indoline and ethylamine) in 40 ml of methanol until the pH is 8. A solution of 5.4 g of cyanamide in 8 ml of water is added and the pH is again adjusted to 8 with aqueous ammonia. After boiling for 12 hours, sulphuric acid is added, with ice-cooling, until the pH is 6. The reaction mixture is evaporated and the residue is crystallized with acetone. This produced 1-ethyl-2-(1-ethyl-guanidinomethyl)-indoline hemisulphate, m.p. 230° C.

EXAMPLES 12 TO 51

The following compounds are obtained analogously to Example 11 from the corresponding 2-alkylaminomethyl-indolines and cyanamide:

12. 2-(1-Methyl-guanidinomethyl)-indoline.
13. 2-(1-Ethyl-guanidinomethyl)-indoline.
14. 2-(1-n-Propyl-guanidinomethyl)-indoline.
15. 2-(1-Isopropyl-guanidinomethyl)-indoline.
16. 2-(1-n-Butyl-guanidinomethyl)-indoline.
17. 2-(1-Isobutyl-guanidinomethyl)-indoline.
18. 2-(1-n-Pentyl-guanidinomethyl)-indoline.
19. 2-(1-Isopentyl-guanidinomethyl)-indoline.
20. 2-(1-n-Hexyl-guanidinomethyl)-indoline.
21. 1-Methyl-2-(1-methyl-guanidinomethyl)-indoline.
22. 1-Methyl-2-(1-ethyl-guanidinomethyl)-indoline.
23. 1-Methyl-2-(1-n-propyl-guanidinomethyl)-indoline.
24. 1-Methyl-2-(1-isopropyl-guanidinomethyl)-indoline.
25. 1-Methyl-2-(1-n-butyl-guanidinomethyl)-indoline.
26. 1-Methyl-2-(1-isobutyl-guanidinomethyl)-indoline.
27. 1-Methyl-2-(1-n-pentyl-guanidinomethyl)-indoline.
28. 1-Methyl-2-(1-isopentyl-guanidinomethyl)-indoline.
29. 1-Methyl-2-(1-n-hexyl-guanidinomethyl)-indoline.
30. 1-Ethyl-2-(1-methyl-guanidinomethyl)-isoindoline.
31. 1-Ethyl-2-(1-n-propyl-guanidinomethyl)-isoindoline.
32. 1-Ethyl-2-(1-isopropyl-guanidinomethyl)-isoindoline.
33. 1-Ethyl-2-(1-n-butyl-guanidinomethyl)-isoindoline.
34. 1-Ethyl-2-(1-isobutyl-guanidinomethyl)-isoindoline.
35. 1-Ethyl-2-(1-n-pentyl-guanidinomethyl)-isoindoline.
36. 1-Ethyl-2-(1-isopentyl-guanidinomethyl)-isoindoline.
37. 1-Ethyl-2-(1-n-hexyl-guanidinomethyl)-isoindoline.
38. 1-n-Propyl-2-(1-methyl-guanidinomethyl)-isoindoline.
39. 1-n-Propyl-2-(1-ethyl-guanidinomethyl)-isoindoline.

40. 1-Isopropyl-2-(1-methyl-guanidinomethyl)-isoindoline.
41. 1-Isopropyl-2-(1-ethyl-guanidinomethyl)-isoindoline.
42. 1-n-Butyl-2-(1-methyl-guanidinomethyl)-isoindoline.
43. 1-n-Butyl-2-(1-ethyl-guanidinomethyl)-isoindoline.
44. 1-Isobutyl-2-(1-methyl-guanidinomethyl)-isoindoline.
45. 1-Isobutyl-2-(1-ethyl-guanidinomethyl)-isoindoline.
46. 1-n-Pentyl-2-(1-methyl-guanidinomethyl)-isoindoline.
47. 1-n-Pentyl-2-(1-ethyl-guanidinomethyl)-isoindoline.
48. 1-Isopentyl-2-(1-methyl-guanidinomethyl)-isoindoline.
49. 1-Isopentyl-2-(1-ethyl-guanidinomethyl)-isoindoline.
50. 1-n-Hexyl-2-(1-methyl-guanidinomethyl)-isoindoline.
51. 1-n-Hexyl-2-(1-ethyl-guanidinomethyl)-isoindoline.

EXAMPLE 52

A mixture of 25.3 g of 1-ethyl-2-ethylaminomethylindoline hemisulphate and 25 g of cyanamide is heated at 120° C. for 20 minutes. After cooling, acetone is added and the mixture is filtered. The crystals are taken up in icecold sodium bicarbonate solution and the aqueous phase is extracted with chloroform. The oily base obtained after drying and evaporating the chloroform phase is dissolved in a little methanol and the pH of the solution is adjusted to 6 with sulphuric acid. The solution is evaporated. The residue is triturated with acetone and 1-ethyl-2-(1-ethyl-guanidinomethyl)-indoline hemisulphate is obtained, m.p. 230° C.

EXAMPLE 53

A solution of 26.5 g of 1-ethyl-2-guanidinomethylindole hemisulphate (obtainable from ethyl indole-2-carboxylate via ethyl 1-ethyl-indole-2-carboxylate, 1-ethyl-2-hydroxymethyl-indole, 1-ethyl-2-chloromethyl-indole, 1-ethyl-2-phthalimidomethyl-indole and 1-ethyl-2-aminomethyl-indole) in a mixture of 300 ml of acetic acid and 70 ml of 2 N sulphuric acid is hydrogenated at 60° C. with 10 g of palladium/barium sulphate (5%) under normal pressure. After the absorption of hydrogen has ceased, the solution is filtered. The filtrate is evaporated and 1-ethyl-2-guanidinomethylindoline hemisulphate is obtained, m.p. 199° C.

EXAMPLE 54

23 g of sodium borohydride are added to a solution of 26.5 g of 1-ethyl-2-guanidinomethyl-indole hemisulphate in 100 ml of acetic acid at 20° C., with stirring. The mixture is heated briefly to 60° C., excess NaBH$_4$ is decomposed with water, the mixture is evaporated, the residue is dissolved in water, the pH of the solution is adjusted to 7 and the solution is extracted with ether. After drying and evaporating the extract, the pH is adjusted to 6 with dilute sulphuric acid, the solution is again evaporated and the residue is crystallized with acetone. This produces 1-ethyl-2-guanidinomethylindoline hemisulphate, m.p. 199° C.

EXAMPLE 55

10 g of 1-benzyl-2-guanidinomethyl-indoline hemisulphate (obtainable from ethyl indoline-2-carboxylate by N-benzylation, reduction and reaction with SOCl$_2$ to give 1-benzyl-2-chloromethyl-indoline, reaction of the latter with potassium phthalimide and hydrolysis of the reaction product, and reaction of this product with S-methyl-isothiourea hemisulphate) are dissolved in 200 ml of ethanol and hydrogenated over 3 g of 5% Pd/C at 20° C. and 1 atmosphere until the reaction ceases. After filtering and evaporating the filtrate, 2-guanidinomethyl-indoline hemisulphate is obtained.

The Examples which follow relate to pharmaceutical formulations which contain guanidines of formula I or their acid addition salts:

EXAMPLE A: TABLETS

A mixture of 1 kg of 1-ethyl-2-guanidinomethyl-indoline sulphate, 4 kg of lactose, 1.2 kg of potato starch, 0.2 kg of talc and 0.1 kg of magnesium stearate is compressed into tablets in conventional fashion, in such a way that each tablet contains 10 mg of active compound.

EXAMPLE B: DRAGEES

Tablets are pressed analogously to Example A and are subsequently coated in the conventional manner with a coating of sucrose, potato starch, talc, tragacanth and a dyestuff.

EXAMPLE C: CAPSULES 5 kg of 1-methyl-2-guanidinomethyl-indoline sulphate are filled in the conventional manner into hard gelatine capsules, so that each capsule contains 20 mg of the active compound.

Tablets, dragees and capulses which contain one or more of the other active compounds of formula I and/or their physiologically acceptable acid addition salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A 2-guanidinomethyl-indoline of the formula

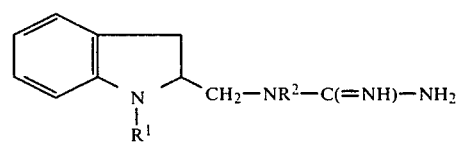

wherein $R^1$ and $R^2$ each independently is H or alkyl of 1–6 carbon atoms, or the physiologically acceptable acid addition salts thereof.

2. 2-Guanidinomethyl-indoline, a compound of claim 1, or the physiologically acceptable acid addition salts thereof.

3. 1-methyl-2-guanidinomethyl-indoline, a compound of claim 1, or the physiologically acceptable acid addition salts thereof.

4. 1-ethyl-2-guanidinomethyl-indoline, a compound of claim 1, or the physiologically acceptable acid addition salts thereof.

5. 1-ethyl-2-(1-ethyl-guanidinomethyl)-indoline, a compound of claim 1, or the physiologically acceptable acid addition salts thereof.

6. A compound of claim 1, wherein $R^1$ and $R^2$ each independently is H or alkyl of 1-3 carbon atoms.

7. A pharmaceutical composition, which comprises an antihypertensively effective amount of a compound of claim 1 and a pharmaceutically acceptable carrier.

8. An antihypertensive pharmaceutical composition which comprises 1–100 mg of a compound of claim 1 and a pharmaceutically acceptable carrier.

9. A method of treating hypertension which comprises administering an antihypertensively effective amount of a compound of claim 1.

10. An indoline derivative of the formula

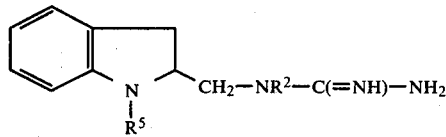

wherein $R^5$ is benzyl, tolylmethyl, diphenylmethyl or carbobenzoxy and $R^2$ is H or alkyl of 1-6 carbon atoms, or the acid addition salts thereof.

* * * * *